(12) United States Patent
Lu et al.

(10) Patent No.: US 10,774,393 B2
(45) Date of Patent: Sep. 15, 2020

(54) CELL SURFACE MARKER DEPLETION IN A SAMPLE PROCESSING DEVICE

(71) Applicant: Roche Molecular Systems, Inc., Pleasanton, CA (US)

(72) Inventors: Jinshuang Lu, Sudbury, MA (US); Beiyang Ma, Southborough, MA (US); Nancy Schoenbrunner, Charlestown, MA (US); Fangnian Wang, Hopkinton, MA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 317 days.

(21) Appl. No.: 15/597,529

(22) Filed: May 17, 2017

(65) Prior Publication Data

US 2017/0335413 A1 Nov. 23, 2017

Related U.S. Application Data

(60) Provisional application No. 62/339,596, filed on May 20, 2016.

(51) Int. Cl.
| | |
|---|---|
| *C12P 19/34* | (2006.01) |
| *C12Q 1/70* | (2006.01) |
| *B01L 3/00* | (2006.01) |
| *C12M 1/33* | (2006.01) |
| *C12Q 1/6834* | (2018.01) |
| *C12Q 1/6886* | (2018.01) |
| *B01L 7/00* | (2006.01) |

(52) U.S. Cl.
CPC .......... *C12Q 1/701* (2013.01); *B01L 3/50273* (2013.01); *C12M 45/02* (2013.01); *C12Q 1/6834* (2013.01); *C12Q 1/6886* (2013.01); *B01L 3/502761* (2013.01); *B01L 7/525* (2013.01); *B01L 2200/0668* (2013.01); *B01L 2300/087* (2013.01); *B01L 2400/0481* (2013.01); *B01L 2400/0683* (2013.01)

(58) Field of Classification Search
CPC ....... B01L 2200/0668; B01L 2300/087; B01L 2400/0481; B01L 2400/0683; B01L 3/50273; B01L 3/502761; B01L 7/525; C12M 45/02; C12Q 1/6834; C12Q 1/6886; C12Q 1/701
See application file for complete search history.

(56) References Cited

U.S. PATENT DOCUMENTS

| | | |
|---|---|---|
| 4,427,580 A | 1/1984 | Kinsella et al. |
| 4,483,920 A | 11/1984 | Gillespie et al. |
| 5,234,809 A | 8/1993 | Boom et al. |
| 5,674,738 A | 10/1997 | Abramson et al. |
| 5,705,628 A | 1/1998 | Hawkins |
| 5,898,071 A | 4/1999 | Hawkins |
| 6,440,725 B1 | 8/2002 | Pourahmadi et al. |
| 6,534,262 B1 | 3/2003 | McKernan et al. |
| 6,783,934 B1 | 8/2004 | McMillan et al. |
| 6,818,185 B1 | 11/2004 | Petersen et al. |
| 6,979,424 B2 | 12/2005 | Northrup et al. |
| 7,718,421 B2 | 5/2010 | Chen et al. |
| 8,580,559 B2 | 11/2013 | Petersen et al. |
| 8,940,526 B2 | 1/2015 | Ririe et al. |
| 9,322,052 B2 | 4/2016 | Petersen et al. |
| 2004/0161788 A1* | 8/2004 | Chen ................. C12N 15/1003 435/6.11 |
| 2010/0005638 A1 | 1/2010 | Fujii |
| 2010/0120129 A1* | 5/2010 | Amshey ............ B01L 3/502715 435/270 |
| 2015/0232955 A1 | 8/2015 | Baum et al. |

FOREIGN PATENT DOCUMENTS

| | | |
|---|---|---|
| EP | 2574400 A1 | 4/2013 |
| WO | 0043551 A1 | 7/2000 |
| WO | 201008097878 A2 | 7/2010 |

OTHER PUBLICATIONS

Chen et al., European Journal of Microbiology and Immunology, 5 (4):236-246, Dec. 4, (Year: 2015).*
Binnicker et al., JCM, 53(7), 23532354, July (Year: 2015).*
International Search Report dated Aug. 9, 2017 in Application No. PCT/EP2017/062191, 10 pages.

* cited by examiner

*Primary Examiner* — Cynthia B Wilder
(74) *Attorney, Agent, or Firm* — Charles M. Doyle; Pamela C. Ancona

(57) ABSTRACT

The disclosure provides methods, devices, and kits for conducting a quantitative analysis of a whole blood sample. Various modifications to the disclosed methods, devices, and kits are described.

16 Claims, 8 Drawing Sheets

| Quant performance in plasma (VL, n=3) | | | |
|---|---|---|---|
| Input | Calculated | Accuracy | Precision |
| 1.70 | 1.75 | 0.05 | 0.45 |
| 2.00 | 2.02 | 0.02 | 0.30 |
| 3.00 | 2.93 | -0.07 | 0.21 |
| 4.00 | 4.05 | 0.05 | 0.03 |
| 5.00 | 5.02 | 0.02 | 0.03 |
| 6.00 | 5.94 | -0.06 | 0.06 |
| 7.00 | 6.98 | -0.02 | 0.13 |

Fig. 4

| LoD | HIV-1 Type | Conc. | Ave Ct | Ct CV% | Hit Rate |
|---|---|---|---|---|---|
| Plasma | HIV-1 M | 100 copies/mL | 33.69 | 3.0% | 23/24 |
| Whole Blood | HIV-1 M | 200 copies/mL | 33.51 | 3.2% | 20/21 |

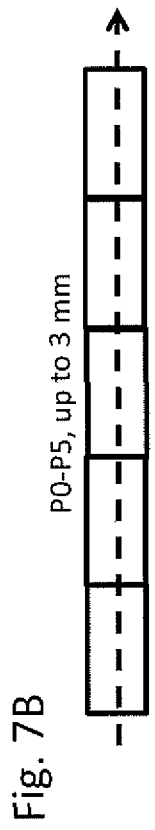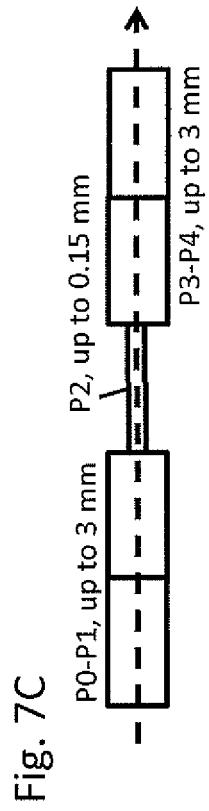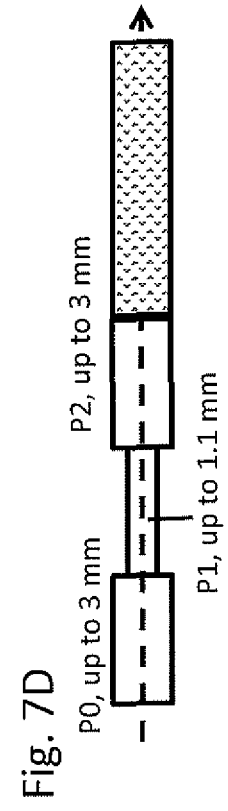
Fig. 7B
Fig. 7C
Fig. 7D
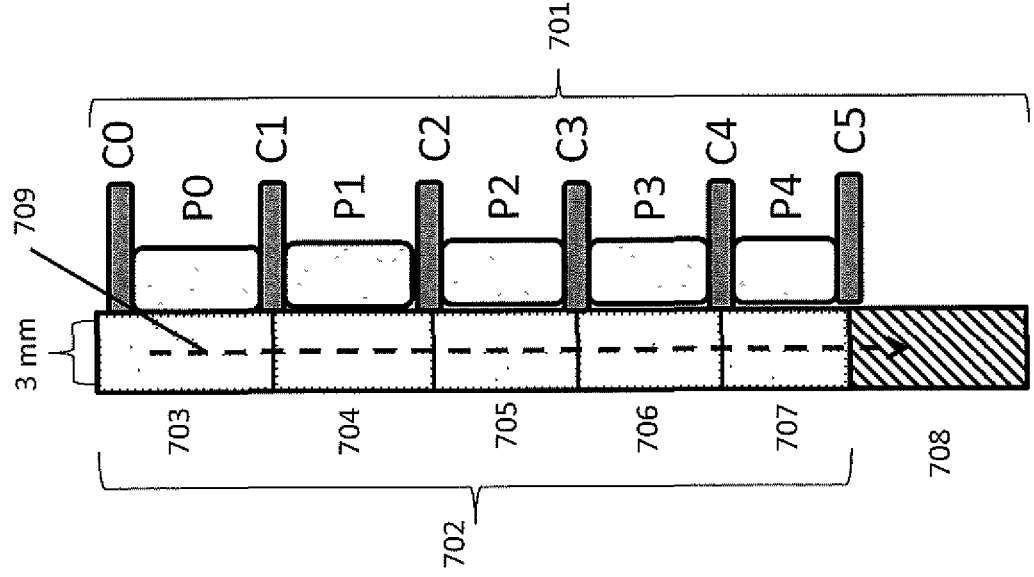
Fig. 7A

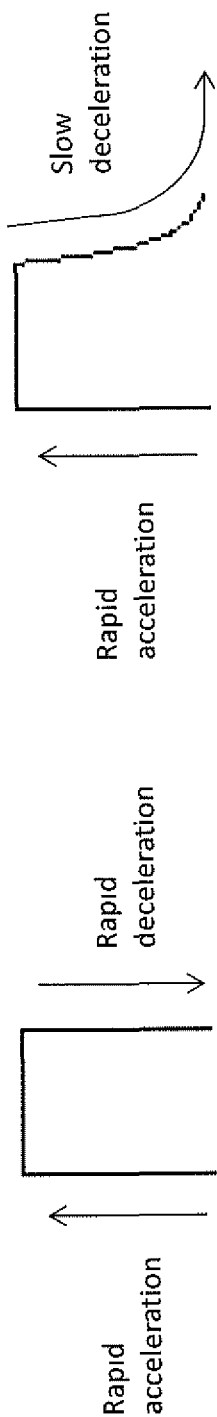

CELL SURFACE MARKER DEPLETION IN A SAMPLE PROCESSING DEVICE

CROSS-REFERENCE TO RELATED APPLICATION

The application claims priority to U.S. Application Ser. No. 62/339,596, filed May 20, 2016, the disclosure of which is incorporated herein by reference.

FIELD OF THE DISCLOSURE

The present disclosure relates to a sample processing device including a plurality of segments and at least one segment configured to perform a cell surface marker-depletion step of a whole blood sample.

BACKGROUND

Currently, quantification of HIV-1 by viral load testing in resource-limited settings is performed in centralized laboratories by PCR-based methods using plasma samples. Dried blood spots have been employed as an alternative sample type, and while such alternatives may be beneficial for various reasons, the suitability of dried blood samples for viral load testing is questionable and depending on the assay used, proviral DNA and intracellular viral RNA present in dried blood spots interferes with RNA quantification.

In resource-limited settings or other field-based testing with unreliable or no access to phlebotomy or lab equipment, the collection and processing of plasma is challenging or impossible. Point of care testing is an alternative that has the potential to facilitate care for the greatest number of patients and point of care devices can be used to analyze whole blood samples easily collected using finger or heel prick and processing without additional instrumentation. However, there is a poor correlation in HIV viral loads measured by RT-PCR for whole blood samples vs. plasma. The T-cell subpopulation of white blood cells in whole blood has HIV proviral DNA, mRNA, and cell-associated virions. Hence, the quantification with whole blood is often higher than with plasma, especially at low titers. This can lead to what would otherwise be a viral load below the clinical threshold of 1e3 copies/ml to greater than 1e3 copies/ml. These results have been observed with fresh and frozen whole blood, as well as dried blood spots.

Because of the difficulties with collecting plasma samples in resource-limited settings, it is desirable to find a solution for a molecular point of care viral load test that gives quantitative results comparable to plasma.

SUMMARY

The methods described herein are used to conduct a quantitative analysis of a whole blood sample for viral or tumor load. The whole blood sample used in the method comprises a plurality of cells including a viral or tumor cell surface marker, and the method comprises: (a) adding the whole blood sample to a device or a component thereof that does not include a filter, wherein the device or component includes a surface including immobilized anti-viral or anti-tumor cell surface marker antibodies; (b) mixing the surface and sample in the device to form a depleted sample, wherein the depleted sample comprises <5% cells including the cell surface marker and the mixing step is performed under conditions that do not lyse cells in the sample; and (c) measuring, in the device, viral or tumor load in the depleted sample.

In a first embodiment, the methods described herein are used to conduct a quantitative analysis of a whole blood sample for tumor load. The whole blood sample used in the method comprises a plurality of cells including a tumor cell surface marker, and the method comprises: (a) adding the whole blood sample to a device or a component thereof that does not include a filter, wherein the device or component includes a surface including immobilized anti-tumor cell surface marker antibodies; (b) mixing the surface and sample in the device to form a depleted sample, wherein the depleted sample comprises <5% cells including the cell surface marker and the mixing step is performed under conditions that do not lyse cells in the sample; and (c) measuring, in the device, tumor load in the depleted sample.

In a second embodiment, the methods described herein are used to conduct a quantitative analysis of a whole blood sample for viral load. The whole blood sample used in the method comprises a plurality of cells including a viral cell surface marker, and the method comprises: (a) adding the whole blood sample to a device or a component thereof that does not include a filter, wherein the device or component includes a surface including immobilized anti-viral cell surface marker antibodies; (b) mixing the surface and sample in the device to form a depleted sample, wherein the depleted sample comprises <5% cells including the cell surface marker and the mixing step is performed under conditions that do not lyse cells in the sample; and (c) measuring, in the device, viral load in the depleted sample.

In a specific embodiment the method is performed in a device configured to perform a nucleic acid analysis of one or more viral or tumor-associated target oligonucleotide sequences, wherein the device comprises a sample pre-treatment compartment lacking a filter and comprising a surface including immobilized anti-viral or anti-tumor cell surface marker antibodies, the method comprising a. adding the whole blood sample to the sample pre-treatment compartment;
b. subjecting the sample pre-treatment compartment to conditions sufficient to mix the surface and sample to form a depleted sample and cell-surface marker cell-bound surface, wherein the depleted sample comprises <5% cells including the viral or tumor cell surface marker and the mixing is performed under conditions that do not lyse cells in the sample;
c. separating the depleted sample from the surface;
d. transferring the depleted sample from the sample pre-treatment compartment to a nucleic acid analysis region in the device;
e. subjecting the depleted sample to the nucleic acid analysis in the device; and
f. detecting, in the device, the one or more target oligonucleotides in the depleted sample; and
g. calculating the viral or tumor load based on the detection step (f).

In one embodiment, the disclosure contemplates a method performed in a device configured to perform a nucleic acid analysis of one or more viral target oligonucleotide sequences, wherein the device comprises a sample pre-treatment compartment lacking a filter and comprising a surface including immobilized anti-viral cell surface marker antibodies, the method comprising a. adding the whole blood sample to the sample pre-treatment compartment;

b. subjecting the sample pre-treatment compartment to conditions sufficient to mix the surface and sample to form a depleted sample and cell-surface marker cell-bound surface, wherein the depleted sample comprises <5% cells including the viral cell surface marker and the mixing is performed under conditions that do not lyse cells in the sample;
c. separating the depleted sample from the surface;
d. transferring the depleted sample from the sample pre-treatment compartment to a nucleic acid analysis region in the device;
e. subjecting the depleted sample to the nucleic acid analysis in the device; and
f. detecting, in the device, the one or more viral target oligonucleotides in the depleted sample; and
g. calculating the viral load based on the detection step (f).

The disclosure also contemplates a method performed in a device configured to perform a nucleic acid analysis of one or more tumor target oligonucleotide sequences, wherein the device comprises a sample pre-treatment compartment lacking a filter and comprising a surface including immobilized anti-tumor cell surface marker antibodies, the method comprising
a. adding the whole blood sample to the sample pre-treatment compartment;
b. subjecting the sample pre-treatment compartment to conditions sufficient to mix the surface and sample to form a depleted sample and cell-surface marker cell-bound surface, wherein the depleted sample comprises <5% cells including the viral cell surface marker and the mixing is performed under conditions that do not lyse cells in the sample;
c. separating the depleted sample from the surface;
d. transferring the depleted sample from the sample pre-treatment compartment to a nucleic acid analysis region in the device;
e. subjecting the depleted sample to the nucleic acid analysis in the device; and
f. detecting, in the device, the one or more tumor target oligonucleotides in the depleted sample; and
g. calculating the tumor load based on the detection step (f).

Also provided is a device configured to perform a quantitative nucleic acid analysis of one or more target oligonucleotide sequences in a whole blood sample comprising a plurality of cells including a cell surface marker, the device comprising (a) a sample pre-treatment compartment lacking a filter and comprising magnetic particles including immobilized cell surface marker antibodies; and (b) a nucleic acid analysis region comprising one or more additional compartments each configured to conduct one or more steps of said nucleic acid analysis comprising reagent preparation, target enrichment, inhibitor removal, nucleic acid extraction, amplification and real-time detection; wherein the sample pre-treatment compartment is configured to generate a depleted sample comprising <5% cells including the cell surface marker.

In a specific embodiment, the plurality of cells includes monocytes and T-cells and said surface binds to the cell surface marker on said monocytes and T-cells. The depleted sample can comprise <2.5% cells, and more specifically <1% cells including the cell surface marker. The method can achieve a limit of detection of <200, and more particularly, <100 copies/mL of target. The cell surface marker is selected from the group consisting of CD4, CD45, beta-microglobulin, or mixtures thereof and the surface can be a particle, e.g., a magnetic particle, or an inner wall of a pre-treatment compartment of the device. The device and method are used to assess the quantity of a target nucleic acid, including but not limited to, the viral load of HIV in a sample, as well as the viral load of other viruses, including but not limited to hepatitis (e.g., hepatitis A (HAV), B (HBV), C (HCV), and E (HEV), and in particular, hepatitis B and C), Epstein-Barr (EBV), West Nile Virus (WNV), Cytomegalovirus (CMV), Japanese Encephalitis (JNV), Chikungunya (CHIK), Dengue Fever, BK Virus, Zika, Babesia, and combinations thereof. In a specific embodiment, the device and method are used to assess the viral load of HIV, HBV, or HCV.

Moreover, provided herein is a method of conducting a quantitative analysis of a whole blood sample for a target nucleic acid, wherein said whole blood sample comprises a plurality of cells including a cell surface marker associated with the target nucleic acid, said method comprising
a. adding said whole blood sample to a device comprising a tube defining a fluid flow channel and comprising a surface including immobilized cell surface marker antibodies;
b. mixing said surface and sample in said device to form a depleted sample, wherein said depleted sample comprises <5% cells including said cell surface marker and said mixing step is performed without a filter in the flow channel and under conditions that do not lyse cells in said sample; and
c. measuring, in said device, the target nucleic acid in said depleted sample.

Also provided is a device configured to perform a quantitative PCR analysis of one or more target oligonucleotide sequences in a whole blood sample comprising a plurality of cells including a cell surface marker, said device comprising a tube defining a fluid flow channel and a plurality of segments positioned therein, said device including
(a) a first set of segments in said fluid flow channel defining a sample pre-treatment compartment comprising, from a proximate to a distal end, a first flanking segment, an inner segment, and a second flanking segment, and anti-cell surface marker antibodies immobilized in one or more of said segments, wherein said sample pre-treatment compartment does not include a filter;
(b) a second set of segments in said fluid flow channel defining a PCR analysis region adjacent to said sample pre-treatment compartment, said PCR analysis region comprising one or more additional segments each configured to conduct one or more steps of said PCR analysis comprising reagent preparation, target enrichment, inhibitor removal, nucleic acid extraction, amplification and real-time detection; and
(c) a plurality of compression members operably connected with said plurality of segments and configured to selectively compress one or more segments of said sample pre-treatment compartment to form a flow channel in the sample pre-treatment compartment such that the inner segment flow channel diameter is less than the diameter of the flow channel in the first and second flanking segments; wherein said device is configured to generate a depleted sample in the sample pre-treatment compartment comprising <5% cells including said cell surface marker.

In this specific embodiment, the device comprises a sample pre-treatment compartment positioned therein, said sample pre-treatment compartment comprising, from a proximate to a distal end, a first flanking segment, an inner segment, and a second flanking segment, and said mixing step comprises selectively compressing one or more segments of said sample pre-treatment compartment to form a flow channel in the sample pre-treatment compartment such that the inner segment flow channel diameter is less than the diameter of the flow channel in the first and second flanking segments. In a particular embodiment, the inner segment flow channel diameter is between 25-50% of the diameter of the flow channel in the first and second flanking segments, and more specifically, the inner segment flow channel diameter is about 33% of the diameter of the diameter of the flow channel in the first and second flanking segments.

BRIEF DESCRIPTION OF THE FIGURES

FIG. 4 shows the limits of detection (LOD) of the Cobas® LIAT® HIV Quantitative assay in plasma and whole blood.

In FIG. 6A, viral load correlation before CD4 antibody particle treatment is shown and in FIG. 6B, viral load correlation after CD4 antibody pre-treatment is shown.

FIGS. 7A-7D show the configuration of the sample pre-treatment compartment of a sample processing device (FIG. 7A) configured to perform conventional lysis (FIG. 7B), harsh lysis (FIG. 7C), and cell depletion (FIG. 7D).

FIGS. 8A-8B show the compression member motor speed used in conventional and harsh lysis (FIG. 8A) versus that used in cell depletion (FIG. 8B).

DETAILED DESCRIPTION

Definitions

Figure 1:
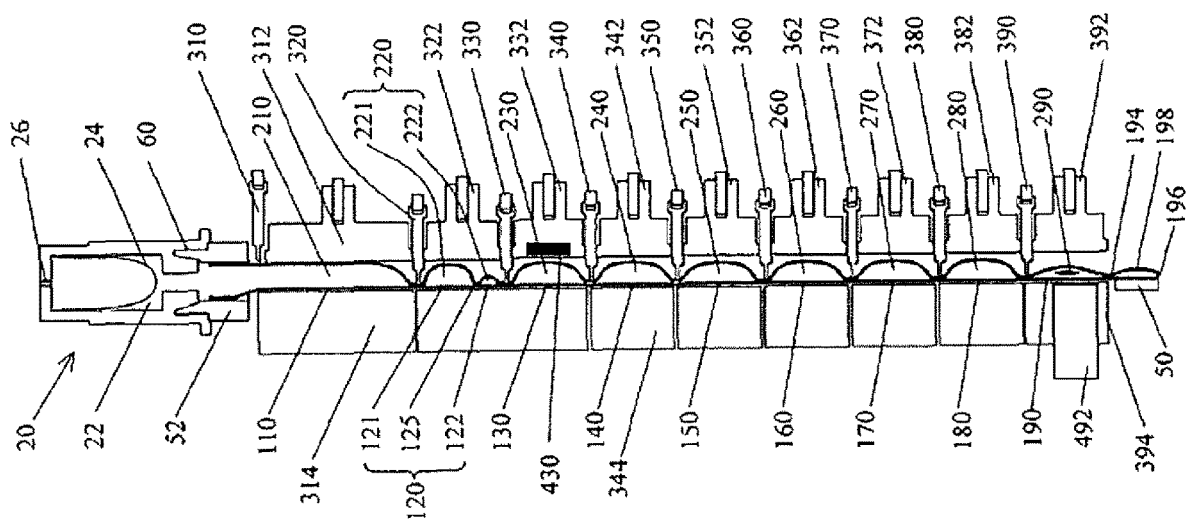
FIG. 1 shows an exemplary sample processing device.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The terms "detect," "detecting," "detection," and similar terms are used in this application to broadly refer to a process or discovering or determining the presence or an absence, as well as a degree, quantity, or level, or probability of occurrence of something. For example, the term "detecting" when used in reference to a target nucleic acid sequence, can denote discovery or determination of the presence, absence, level or quantity, as well as a probability or likelihood of the presence or absence of the sequence. It is to be understood that the expressions "detecting presence or absence," "detection of presence or absence" and related expressions include qualitative and quantitative detection. For example, quantitative detection includes the determination of level, quantity or amounts of HIV-associated nucleic acid sequences in a sample.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence. This region of is typically about 15 to about 40 nucleotides in length. A "primer pair" refers to a forward primer and reverse primer (sometimes called 5' and 3' primers) that are complementary to opposite strands of a target sequence and designed to amplify the target sequence. The forward and reverse primers are arranged within an amplifiable distance of each other on the target sequence, e.g., about 10-5000 nucleotides, or about 25-500 nucleotides.

As used herein, "probe" means any molecule that is capable of selectively binding to a specifically intended target biomolecule, for example, a nucleic acid sequence of interest to be bound, captured or hybridized by the probe.

The words "complementary" or "complementarity" refer to the ability of a nucleic acid in a polynucleotide to form a base pair with another nucleic acid in a second polynucleotide. For example, the sequence 5'-A-G-T-3' (5'-A-G-U-3' for RNA) is complementary to the sequence 3'-T-C-A-5' (3'-U-C-A-5' for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The term "amplification conditions" or similar expressions refer to conditions in a nucleic acid amplification reaction (e.g., PCR amplification) that allow for hybridization and template-dependent extension of the primers. The term "amplicon" refers to a nucleic acid molecule that contains all or a fragment of the target nucleic acid sequence and that is formed as the product of in vitro amplification by any suitable amplification method. Various PCR conditions are described in PCR Strategies (Innis et al., 1995, Academic Press, San Diego, Calif.) at Chapter 14; PCR Protocols: A Guide to Methods and Applications (Innis et al., Academic Press, NY, 1990)

The term "thermostable nucleic acid polymerase" or "thermostable polymerase" refers to a polymerase enzyme, which is relatively stable at elevated temperatures when compared, for example, to polymerases from *E. coli*. A thermostable polymerase is suitable for use under temperature cycling conditions typical of the polymerase chain reaction ("PCR"). Exemplary thermostable polymerases include those from *Thermus thermophilus, Thermus caldophilus, Thermus* sp. Z05 (see, e.g., U.S. Pat. No. 5,674,738) and mutants of the *Thermus* sp. ZO5 polymerase, *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Thermotoga maritima, Thermotoga neapolitana* and *Thermosipho africanus*, and modified versions thereof.

The term "sample" or "biological sample" refers to any composition containing or presumed to contain nucleic acid from an individual. The term includes purified or separated components of cells, tissues, or blood, e.g., DNA, RNA, proteins, cell-free portions, or cell lysates. In a specific embodiment, analysis is conducted on whole blood samples. As used herein, a "whole blood sample" includes blood drawn from the body from which no constituent, such as plasma or platelets, has been removed. Generally, the sample is unmodified except for the presence of an anticoagulant. A sample can also refer to other types of biological samples, e.g., plasma, serum, blood components (buffy coat), and dried blood spots. Samples also may include constituents and components of in vitro cultures of cells obtained from an individual, including cell lines.

The term "kit" refers to any manufacture (e.g., a package or a container) including at least one device comprising a solid support, as described herein for specifically amplifying, capturing, tagging/converting or detecting a target nucleic acid sequence as described herein. The kit can further include instructions for use, supplemental reagents and/or components or modules used in the method described herein or a step thereof.

Methods

This disclosure provides a method of conducting a quantitative analysis of a whole blood sample for a target nucleic acid sequence, wherein the sample comprises a plurality of cells including a cell surface marker. In a particular embodiment, the target nucleic acid sequence is viral and the cell surface marker is a viral cell surface marker. The method includes the following steps:

a. adding the whole blood sample to a device comprising a surface including immobilized anti-cell surface marker antibodies;

b. mixing the surface and sample in the device to form a depleted sample, wherein the depleted sample comprises <5% cells including the cell surface marker and the mixing step is performed under conditions that do not lyse cells in the sample; and c. measuring, in the device, amount of target nucleic acid sequence in the depleted sample.

If the target nucleic acid sequence is viral, the amount of target nucleic acid sequence in the depleted sample is correlated with the viral load in the sample. Alternatively, if the target nucleic acid sequence is associated with a tumor, an anti-tumor cell surface marker antibody is used on the surface in step (a), and the amount of target nucleic acid sequence in the deplete sample is correlated with the tumor load in the sample.

In a particular embodiment, the mixing step is performed without filtering the cell surface markers from the sample.

The whole blood samples tested in the methods described herein comprise a plurality of cell types that include a cell surface marker, including but not limited to monocytes and T-cells, as well as macrophages and dendritic cells. In a specific embodiment, the plurality of cells includes monocytes and T-cells.

In a specific embodiment, the methods and devices described herein are used to analyze HIV viral load and the HIV infected cell marker used in the methods described herein can be CD4, CD45, beta-microglobulin, or combinations thereof. In a specific embodiment, the HIV infected cell marker is CD4. Additional HIV infected markers can include but are not limited to CD27, TNFR-II, IL-12, and/or CD38. The devices and methods are used to assess the viral load of HIV, as well as other viruses, including but not limited to hepatitis (e.g., hepatitis A (HAV), B (HBV), C (HCV), and E (HEV), and in particular, hepatitis B and C), Epstein-Barr (EBV), West Nile Virus (WNV), Cytomegalovirus (CMV), Japanese Encephalitis (JNV), Chikungunya (CHIK), Dengue Fever, BK Virus, Zika, Babesia, and combinations thereof. In a specific embodiment, the device and method are used to assess the viral load of HIV, HBV, or HCV.

Moreover, the devices and methods described herein can also be used to assess the amount of any target nucleic acid sequence, wherein the presence of target sequence is associated with a given cell surface marker. A cell surface marker is a protein expressed on the surface of cells that serve as markers of specific cell types characteristic of a particular disease state or condition in a patient. For example, a viral cell surface marker is a marker of a viral infection, and likewise, tumor cell markers are markers of different forms of cancer. If a viral cell marker is under evaluation, viral load is assessed in the sample, whereas if a tumor cell marker is under evaluation, tumor load is assessed in the sample. Common tumor markers, include but are not limited to: ALK, AFP, B2M, Beta-hCG, BRCA1, BRCA2, BCR-ABL, BRAF V600 mutations, C-kit/CD117, CA15-3/CA27.29, CA19-9, CA-125, calcitonin, CEA, CD20, CgA, circulating tumor cells of epithelial origin, Cytokeratin fragment 21-1, EGFR, ER, PR, fibrin, fibrinogen, HE4, HER2/neu, IgGs, KRAS, lactate dehydrogenase, NSE, nuclear matrix protein 22, PD-L1, PSA, thyroglobulin, uPA, and combinations thereof. In addition, other cell markers characteristics of a given disease or condition can also be analyzed using the methods described herein. For example, fetal genetic markers can be detected in maternal plasma using the methods and devices described herein.

The methods and devices described herein may employ antibodies or other binding reagents specific for a cell surface receptor of a virus. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. J. Cell Physiol., 67 (Suppl); 51-64 (1966) and Hochman, 1. Inbar, D. and Givol, D. Biochemistry 12: 1130 (1973)), as well as antibody constructs that have been chemically modified. The antibodies used herein may be monoclonal or polyclonal. In a specific embodiment, the antibodies are monoclonal. Additionally or alternatively, the methods and devices can employ other binding reagents having binding specificity for a viral cell surface receptor. The binding reagents can be naturally derived, or wholly or partially synthetic, and include, without limitation, a ligand, enzyme, oligonucleotide, or aptamer.

Accordingly, the surfaces described herein include a plurality of binding reagents for a cell surface marker. In one embodiment, the cell surface marker is an HIV infected cell marker, including but not limited to, an anti-CD4, anti-CD45, anti-beta-microglobulin, anti-CD27, anti-TNFR-II, anti-IL-12, and/or anti-CD38. In another exemplary embodiment, the cell surface marker is a tumor marker, including but not limited to anti-ALK, anti-AFP, anti-B2M, anti-Beta-hCG, anti-BRCA1, anti-BRCA2, anti-BCR-ABL, anti-BRAF V600 mutations, anti-C-kit/CD117, anti-CA15-3/CA27.29, anti-CA19-9, anti-CA-125, anti-calcitonin, anti-CEA, anti-CD20, anti-CgA, anti-circulating tumor cells of epithelial origin, anti-Cytokeratin fragment 21-1, anti-EGFR, anti-ER, anti-PR, anti-fibrin, anti-fibrinogen, anti-HE4, anti-HER2/neu, anti-IgGs, anti-KRAS, anti-lactate dehydrogenase, anti-NSE, anti-nuclear matrix protein 22, anti-PD-L1, anti-PSA, anti-thyroglobulin, or anti-uPA. In a specific embodiment, the particles include a plurality, e.g., two or more, different cell markers, e.g., two or more of the following: anti-CD4, anti-CD45, anti-beta-microglobulin, anti-CD27, anti-TNFR-II, anti-IL-12, and/or anti-CD38; or two or more of the following: anti-ALK, anti-AFP, anti-B2M, anti-Beta-hCG, anti-BRCA1, anti-BRCA2, anti-BCR-ABL, anti-BRAF V600 mutations, anti-C-kit/CD117, anti-CA15-3/CA27.29, anti-CA19-9, anti-CA-125, anti-calcitonin, anti-CEA, anti-CD20, anti-CgA, anti-circulating tumor cells of epithelial origin, anti-Cytokeratin fragment 21-1, anti-EGFR, anti-ER, anti-PR, anti-fibrin, anti-fibrinogen, anti-HE4, anti-HER2/neu, anti-IgGs, anti-KRAS, anti-lactate dehydrogenase, anti-NSE, anti-nuclear matrix protein 22, anti-PD-L1, anti-PSA, anti-thyroglobulin, or anti-uPA.

More specifically, the surface includes a plurality of two or more of the following: anti-CD4, anti-CD45, and/or anti-beta-microglobulin. Alternatively, the surface includes a uniform population of anti-HIV infected cells markers. In a particular embodiment, the surface includes a plurality of anti-CD4 antibodies; or a plurality of anti-CD45 antibodies; or a plurality of anti-beta-microglobulin antibodies.

Suitable surfaces includes beads or particles, as well as binding surfaces positioned on the inner, solution facing wall of a compartment, e.g., a pre-treatment compartment, of a device in which the method is conducted. In one embodiment, the surface includes beads or particles such as particles (including but not limited to colloids or beads) commonly used in other types of particle-based assays, e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Particles may be inanimate or alternatively, may include animate biological entities such as cells, viruses, bacterium and the like.

The particles used in the present method may be comprised of any material suitable for attachment to one or more binding reagents, and that may be collected via, e.g., centrifugation, gravity, filtration or magnetic collection. A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles.

The particles may have a wide variety of sizes and shapes. By way of example and not limitation, particles may be between 5 nanometers and 100 micrometers. For example, particles have sizes between 20 nm and 10 micrometers. In a particular embodiment, the particles are 0.1 um to 10 um, and more specifically, up to 5 um. For example, the particles are between 1-5 um. The particles may be spherical, oblong, rod-like, etc., or they may be irregular in shape.

In alternative embodiment, the device used to conduct the method described herein includes a surface that has been modified to include a plurality of immobilized binding reagents for a viral surface marker. In this embodiment, the method comprises adding a whole blood sample to a sample pre-treatment compartment comprising an inner sample facing wall having a plurality of binding reagents for a viral infected cell surface marker immobilized thereon. The pre-treatment compartment is then subjected to conditions sufficient to form a depleted sample and a surface comprising immobilized viral surface marker cells, such that the depleted sample comprises <5% cells including the viral cell surface marker. In a specific embodiment, the subjecting step is performed under conditions that do not lyse cells in the sample. The depleted sample is then separated from the pre-treatment compartment and transferred to a nucleic acid analysis region, as described in more detail below.

The methods described herein can be used to analyze any pathogenic strain of HIV, including HIV-1 and HIV-2, and any group or subtype thereof. For example, the methods can be used to analyze HIV-1 group(s) M, N, O, P, and combinations thereof. In a specific example, the methods are used to analyze HIV-1 group M and/or O, and optionally one or more additional HIV-1 groups. The methods can also be used to analyze one or more subtypes of HIV-1, including but not limited to subtypes, A, A1, A2, CRF19, B, C, D, F, G, CRF02_AG, H, CRF04_cpx, J, K, and combinations thereof. In addition, the methods can also be used to detect HIV-2, groups A-H, and in particular, HIV-2 groups A and B. Moreover, the methods can also be used to detect hepatitis B, hepatitis C, or CMV.

In a specific embodiment, the methods described herein are designed to produce a depleted sample comprising <10% cells having the cell surface marker. More particularly, the depleted sample comprises <5% cells having the cell surface marker, more specifically <3% cells, and even more particularly, <1% cells having the cell surface marker. In a further specific embodiment, the methods described herein can achieve a whole blood viral and/or tumor load of less than 1e3 copies/ml.

Sample Processing Device

The methods described herein are implemented in a sample processing device configured to perform a nucleic acid amplification technique. Nucleic acids extracted from the biological samples may be further processed by amplifying the nucleic acids using at least one of the following exemplary methods: polymerase chain reaction (PCR), rolling circle amplification (RCA), ligase chain reaction (LCR), transcription mediated amplification (TMA), nucleic acid sequence based amplification (NASBA), and strand displacement amplification reaction (SDAR). In some embodiments, the nucleic acids extracted from the organism can be ribonucleic acids (RNA) and their processing may include a coupled reverse transcription and polymerase chain reaction (RT-PCR) using combinations of enzymes such as Tth polymerase and Taq polymerase or reverse transcriptase and Taq polymerase. In some embodiments, nicked circular nucleic acid probes can be circularized using T4 DNA ligase or AMPLIGASE® thermostable DNA ligase (Epicentre Technologies, Madison, Wis., USA) and guide nucleic acids, such as DNA or RNA targets, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TAQMAN® probes (Roche Molecular Systems, Pleasanton, Calif., USA), molecular beacons, fluorescence resonance energy transfer (FRET) probes, SCORPION® probes (Qiagen, Venlo, Netherlands)) and generally use fluorescence quenching as well as the release of quenching or fluorescence energy transfer from one reporter to another to detect the synthesis or presence of specific nucleic acids.

In one embodiment, the methods disclosed herein are implemented in a device comprising self-contained microscale to macroscale channels, chambers, reservoirs, detection and processing regions. The device can be a cartridge, device, container, or pouch, e.g., as described in U.S. Pat. Nos. 6,440,725; 6,783,934; 6,818,185; 6,979,424; 8,580,559; and 8,940,526, the disclosures of which are incorporated herein by reference in their entireties, as well as devices such as those available from Cepheid Corp., Idaho Technology, Inc., and/or Biofire Diagnostics, Inc.

For example, the methods described herein can be implemented in a self-contained nucleic acid analysis pouch which includes a cell lysis zone, a nucleic acid preparation zone, a first-stage amplification zone, a second-stage amplification zone, as shown in FIG. 1 of U.S. Application Publication No. 201000056383, the disclosure of which is incorporated herein by reference. The pouch comprises a variety of channels and blisters of various sizes and is arranged such that the sample flows through the system and various zones and processed accordingly. Sample processing occurs in various blisters located within the pouch. Numerous channels are provided to move the sample within and between processing zones, while other channels are provided to deliver fluids and reagents to the sample or to remove such fluids and reagents from the sample. Liquid within the pouch is moved between blisters by pressure, e.g., pneumatic pressure. In a specific embodiment, the cell-depletion step described herein is performed in a zone preceding the cell lysis zone.

In an alternative example, the methods described herein can be implemented in a self-contained nucleic acid analysis cartridge as shown in FIGS. 3-5 and 9 of U.S. Pat. No. 9,322,052, which is incorporated herein by reference. The cartridge includes, inter alia, multiple chambers comprising a sample chamber for holding a fluid sample introduced through the inlet port, a wash chamber for holding a wash solution, a reagent chamber for holding a lysing reagent, a lysis chamber, a waste chamber for receiving used sample and wash solution, a neutralizer chamber for holding a neutralizer, and a master mix chamber for holding a master mix (e.g., amplification reagents and fluorescent probes) and for mixing the reagents and probes with analyte separated from the fluid sample, a reaction vessel, and a detection chamber. In this particular embodiment, the cell-depletion step described herein is performed in a chamber preceding the lysis chamber.

In a specific embodiment, the methods described herein are conducted in a sample processing device such as that described in U.S. Pat. No. 7,718,421, the disclosure of which is incorporated herein by reference. Segmented devices, such as those described in U.S. Pat. No. 7,718,421, provide a convenient vessel for receiving, storing, processing, and/or analyzing a biological sample. In certain embodiments, the segmented device facilitates sample processing protocols involving multiple processing steps. In certain embodiments, a sample may be collected in a sample device, and the device is then positioned in an analyzer which manipulates the device and its contents to process the sample.

A particular embodiment includes a flexible device which has been segmented into compartments by breakable seals. The individual segments may contain various reagents and buffers for processing a sample. Clamps and actuators may be applied to the device in various combinations and with various timings to direct the movement of fluid and to cause the breakable seals to burst. This bursting of the breakable seals may leave an inner device surface that is substantially free of obstructions to fluid flow. In one embodiment, the flow of the biological sample may be directed toward the distal end of the device as the processing progresses, while the flow of waste may be forced to move in the opposite direction, toward the opening of the device where the sample was initially input. This sample inlet can be sealed, possibly permanently, by a cap with a locking mechanism, and a waste chamber may be located in the cap to receive the waste for storage. A significant benefit of this approach is that the processed sample does not come into contact with surfaces that have been touched by the unprocessed sample. Consequently, trace amounts of reaction inhibitors present in the unprocessed sample that might coat the walls of the device are less likely to contaminate the processed sample.

The sample processing device is shown in FIG. 1 and may include a transparent flexible device 10 capable of being configured into a plurality of segments, such as 16, 110, 120, 130, 140, 150, 160, 170, 180, and/or 190, and being substantially flattened by compression. In an embodiment, a device may have at least two segments. In an embodiment, a device may have at least three segments. The flexible device can provide operational functionality between approximately 2-105° C., compatibility with samples, targets and reagents, low gas permeability, minimal fluorescence properties, and/or resilience during repeated compression and flexure cycles. The device may be made of a variety of materials, examples of which include but are not limited to: polyolefins such as polypropylene or polyethylene, polyurethane, polyolefin co-polymers and/or other materials providing suitable characteristics.

In an additional embodiment, a filter can be embedded in a device segment. In one embodiment, a filter can be formed by stacking multiple layers of flexible filter material. The uppermost layer of the filter that directly contacts a sample may have a pore size selected for filtration; the bottom layer of the filter may include a material with much larger pore size to provide a support structure for the uppermost layer when a pressure is applied during filtration. In this preferred embodiment, the filter may be folded to form a bag, with the edges of its open end firmly attached to the device wall. The segment with the filter bag may be capable of being substantially flattened by compressing the exterior of the device.

In a specific embodiment, the sample pre-treatment compartment does not include a filter.

Moreover, the sample inlet of the device can be adapted to receive a cell-depletion module including a viral infected cell marker immobilization matrix or media that binds to viral cell markers in the sample, allowing a depleted sample to flow through the matrix or media and flow into the sample inlet of the device. Such a module can be used to carry out the cell depletion method with manual mixing of the media/sample.

In exemplary embodiments, one or more reagents can be stored either as dry substance and/or as liquid solutions in device segments. In embodiments where reagents may be stored in dry format, liquid solutions can be stored in adjoining segments to facilitate the reconstitution of the reagent solution. Examples of typical reagents include: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, and phosphothioate nucleic acid probes. In embodiments where one of the reagents is a chaotropic salt solution, a preferred component is guanidinium isocyanate or guanidinium hydrochloride or a combination thereof. In some embodiments, the order in which reagents may be stored in the device relative to the opening through which a sample is input, reflects the order in which the reagents can be used in methods utilizing the tube. In preferred embodiments, a reagent includes a substance capable of specific binding to a preselected component of a sample. For example, a substance may specifically bind to nucleic acid, or a nucleic acid probe may specifically bind to nucleic acids having particular base sequences.

In a specific embodiment, in addition to the depletion surfaces discussed above, the device can also include a substrate such as a particle or a plurality of particles to facilitate the selective adsorption of nucleic acids. The particles are for example, of silica particles, magnetic particles, silica magnetic particles, glass particles, nitrocellulose colloid particles, and magnetized nitrocellulose colloid particles. In some embodiments where the particles can be paramagnetic, the particles can be captured by a magnetic field. Examples of reagents that may permit the selective adsorption of nucleic acid molecules to a functional group-coated surface are described, for example, in U.S. Pat. Nos. 5,705,628; 5,898,071; and 6,534,262, hereby incorporated herein by reference. Separation can be accomplished by manipulating the ionic strength and polyalkylene glycol concentration of the solution to selectively precipitate, and reversibly adsorb, the nucleic acids to a solid phase surface. When these solid phase surfaces are paramagnetic microparticles, the magnetic particles, to which the target nucleic acid molecules have been adsorbed, can be washed under conditions that retain the nucleic acids but not other molecules. The nucleic acid molecules isolated through this process are suitable for: capillary electrophoresis, nucleotide sequencing, reverse transcription, cloning, transfection, transduction, microinjection of mammalian cells, gene therapy protocols, the in vitro synthesis of RNA probes, cDNA library construction, and the polymerase chain reaction (PCR) amplification. Several companies offer magnetic-based purification systems, such as MAGATTRACT® (Qiagen GmbH, Hilden, GERMANY), MAGAZORB® (Cortex Biochem, San Leandro, Calif.), and MAGNA PURE® LC (Roche Diagnostics Operations, Inc., Indianapolis, Ind.). These products use negatively charged particles and manipulate buffer conditions to selectively bind a variety of nucleic acids to the particles, wash the particles and elute the particles in aqueous buffers. Many of the products used by these companies use chaotropic salts to aid in the precipitation of nucleic acids onto the magnetic particles. Examples are described in U.S. Pat. Nos. 4,427,580; 4,483,920; and 5,234,809, hereby incorporated herein by reference.

Preferred exemplary embodiments may include a linear arrangement of 2 or more device segments 110, 120, 130, 140, 150, 160, 170, 180, and/or 190 (FIG. 1). A linear arrangement facilitates moving the sample and resultant waste and target through the tube in a controlled manner. A sample, e.g., a whole blood sample, can be input through a first opening 12 in a first segment 110 of the device. Thereafter, waste from a processed sample can be moved back toward the first opening while the target is pushed towards the opposite end, thereby minimizing contamination of the target by reaction inhibitors that may have become attached to the device wall, and confining the target to a clean segment of the device which can contain suitable reagents for further operations of the target. Some embodiments may use a plurality of segments, each containing at least one reagent. In some embodiments, these segments may contain reagents in the following order: the second segment can include depletion particles and/or a surface comprising an immobilized binding reagent and a dilution buffer; the third segment can be partitioned into two subsections, the first including proteinase K and the second including silica magnetic beads or other suitable particle; the reagent in the fourth segment may be either a lysis reagent; the reagent in the fifth segment may be either a washing buffer; the reagent in the sixth-eighth segments may be a wash buffer, a neutralization reagent, a suspension buffer, an elution reagent, or nucleic acid amplification and detection reagents. In some embodiments, the segments may be arranged continuously, while in other embodiments, these segments may be separated by another segment or segments in between.

In some embodiments, a method of extracting nucleic acids from biological samples by using the apparatus described in the previous paragraphs is contemplated. In certain embodiments, the sequence of events in such a test may include: 1) a biological sample collected with a collection tool, 2) a flexible device, which can include a plurality of segments that may contain the reagents required during the test, and in which the collected sample can be placed using a first opening in the device, 3) at least one substrate that may be set at a controlled temperature and/or other conditions to capture target organisms or nucleic acids during a set incubation period, 4) organisms or molecules, in the unprocessed sample, that may not bind to the substrate and could thus be removed by transferring liquid to a waste reservoir, 5) storing waste, in a waste reservoir, that can be segregated from the target by a clamp and/or actuator compressed against the device, 6) a wash buffer, released from another segment of the device, that can remove reaction inhibitors, 7) an elution reagent, from another segment, that can release the target bound to the substrate after incubation at a controlled temperature, and 8) nucleic acids that can be detected by techniques well known to those familiar in the art or collected through a second opening in the device. In exemplary embodiments the flow of the sample may be from the first opening towards the distal end of the device as the test progresses while the flow of waste may be towards the closed sample input opening of the device, where a waste chamber in the cap of the device receives the waste for storage. Consequently, undesirable contact between a processed sample and surfaces in a reaction vessel that have been touched by the unprocessed sample is avoided, thereby preventing reaction inhibition due to trace amounts of reaction inhibitors present in the unprocessed sample and that might coat the walls of the reaction vessel.

Some embodiments may incorporate the use of a test tube 1, with a flexible device 10 divided into a plurality of segments, such as segments 16, 110, 120, 130, 140, 150, 160, 170, 180, and/or 190, that may be transverse to the longitudinal axis of the device, and which may contain reagents, such as reagents 210, 221, 222, 230, 240, 250, 260, 270, 280, and/or 290; as well as an analyzer, that may have a plurality of compression members, such as actuators 312, 322, 332, 342, 352, 362, 372, 382, and/or 392, clamps, such as clamps 310, 320, 330, 340, 350, 360, 370, 380, and/or 390, and blocks, for example 314, 344, and/or 394 (others unnumbered for simplicity); opposing the actuators and clamps, to process a sample. Various combinations of these actuators, clamps, and/or blocks may be used to effectively clamp the device closed thereby segregating fluid. In exemplary embodiments, at least one of the actuators or blocks may have a thermal control element to control the temperature of a device segment for sample processing. The sample processing apparatus can further have at least one magnetic field source 430 capable of applying a magnetic field to a segment. The sample processing apparatus can further have a detection device 492, such as photometer or a CCD, to monitor a reaction taking place or completed within the device.

Fluid can be driven through a flow-channel by compressing the device with a centrally-positioned actuator, and its flanking clamps if any, to form a flow channel with a gap of about 1 to about 500 um, preferably about 5 to about 500 um through each segment. The adjacent actuators gently compress the adjacent segments in liquid communication with the flow-channel to generate an offset inner pressure to ensure a substantially uniform gap of the flow channel. The two flanking actuators can then alternatively compress and release pressure on the device on their respective segments to generate flow at a controlled flow rate. Optional flow, pressure, and/or force sensors may be incorporated to enable closed-loop control of the flow behavior. The flow-channel process can be used in washing, enhancing the substrate binding efficiency, and detection.

A particle immobilization and re-suspension process can be used to separate the particles from the sample liquid. The magnetic field generated by a magnetic source 430 (FIG. 1) may be applied to a segment containing a magnetic particle suspension to capture and immobilize the particles to the tube wall. An agitation process can be used during the capturing process. In another embodiment, a flow-channel can be formed in the segment with the applied magnetic field, and magnetic particles can be captured in the flow to increase the capturing efficiency. To resuspend immobilized particles, the magnetic field may be turned off or removed, and an agitation or flow-channel process can be used for re-suspension.

In certain embodiments, nucleic acids extracted from the biological samples may be further processed by amplifying the nucleic acids using at least one method from the group: polymerase chain reaction (PCR), rolling circle amplification (RCA), ligase chain reaction (LCR), transcription mediated amplification (TMA), nucleic acid sequence based amplification (NASBA), and strand displacement amplification reaction (SDAR). In some embodiments, the nucleic acids extracted from the organism can be ribonucleic acids (RNA) and their processing may include a coupled reverse transcription and polymerase chain reaction (RT-PCR) using combinations of enzymes such as Tth polymerase and Taq polymerase or reverse transcriptase and Taq polymerase. In some embodiments, nicked circular nucleic acid probes can be circularized using T4 DNA ligase or AMPLIGASE® thermostable DNA ligase and guide nucleic acids, such as DNA or RNA targets, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TAQMAN® probes, molecular beacons, fluorescence resonance energy transfer (FRET) probes, SCORPION® probes) and generally use fluorescence quenching as well as the release of quenching or fluorescence energy transfer from one reporter to another to detect the synthesis or presence of specific nucleic acids.

A real-time detection of a signal from a device segment can be achieved by using a sensor 492 (FIG. 1), such as a photometer, a spectrometer, a CCD, connected to a block, such as block 490. In exemplary embodiments, pressure can be applied by an actuator 392 on the device segment 190 to suitably define the device segment's shape. The format of signal can be an intensity of a light at certain wavelength, such as a fluorescent light, a spectrum, and/or an image, such as image of cells or manmade elements such as quantum dots. For fluorescence detection, an excitation of light from the optical system can be used to illuminate a reaction, and emission light can be detected by the photometer. To detect a plurality of signals having specific wavelengths, different wavelength signals can be detected in series or parallel by dedicated detection channels or a spectrometer.

Kits

In some embodiments, reagents, materials, and devices for carrying out the presently disclosed methods are included in a kit. In some embodiments, the kit includes components for obtaining, storing, and/or preparing sample. Such components include, e.g., sterile needles and syringes, depletion modules, EDTA-lined tubes, buffers (e.g., for binding nucleic acid to, and elution from a matrix), RNase inhibitors, and/or DNase, etc.

In addition, the kit includes an assay processing device such as that described above and optionally, one or more components for obtaining, storing, and/or preparing sample, including but not limited to a depletion module as described hereinabove. In a specific embodiment, the assay processing device includes various reagents required to perform the methods disclosed herein stored within one or more segments of the device.

The kit can further include controls, e.g., a polynucleotide that is wild type at the sequence to be detected, or a polynucleotide that includes the sequence to be detected.

The kit can also include additional devices such as sample tubes or vials; reaction containers (e.g., tubes, multiwell plates, microfluidic chips or chambers, etc), as well as directions for use or reference to a website.

EXAMPLES

Example 1. Viral RNA Isolation and Detection from Whole Blood

RNA isolation and RNA sequence detection can be accomplished in a tube 1 (FIG. 1), including a flexible device having nine segments separated by peelable seals and containing pre-packed reagents, and a cap, having a waste reservoir housed therein. Fluid flow from one segment or subsection of the device to another is controlled as described herein by selective engagement of one or more actuators and clamps operably connected within one or more segments or subsections of the device. The first segment of the device can receive the whole blood sample. The second segment contains 560 ug of DYNABEADS® magnetic glass particles (Dynal/Invitrogen, Carlsbad, Calif.) conjugated to anti-CD4 antibodies suspended in dilution buffer having 100 ul of phosphate buffered saline (PBS) (137 mM NaCl, 2.7 mM KCl, 4.3 mM $Na_2HPO_4$, 1.4 mM $KH_2PO_4$, pH 7.3). The $3^{rd}$ segment contains the quantification standard. The $4^{th}$ segment is partitioned into two subsections, the 1st subsection containing 200 ug proteinase K, and the 2nd subsection including 250 ug Silica Magnetic particles, wherein the subsections are separated by a peelable seal. The $5^{th}$ segment contains 200 ul of lysis buffer comprising chaotropic salts which contain 4.7 M guanidinium hydrochloride, 10 mM urea, 10 mM Tris HCl, pH 5.7, and 2% TRITON® X-100 (Union-Carbide Corporation, Seadrift, Tex.). The $6^{th}$ segment contains 80 ul of wash buffer (including, e.g., 50% ethanol, 20 mM NaCl, 10 mM Tris HCl, pH 7.5). The $7^{th}$ segment contains 80 ul of 20 mM 2-morpholinoethanesulfonic acid (MES) buffer, pH 5.3. The pH of the MES buffer is adjusted such that it can be low enough to avoid DNA elution from the particles. The $8^{th}$ segment contains 40 ul elution buffer (e.g., 10 mM Tris HCl, pH 8.5, or any buffer suitable for PCR). The pH of the elution buffer is adjusted such that it can be high enough to elute the DNA from the surface of the particles into the buffer. The $9^{th}$ segment contains PCR reagents (which can contain 10 nmol of each one of: dATP, dCTP, and dGTP; 20 nmol dUTP, 2.5 mmol of KCl, 200 nmol of $MgCl_2$, 1-5 units of Taq DNA polymerase, 1-5 units of Tth DNA polymerase, 20-100 pmol of each of the oligonucleotide primers, and 6-25 pmol of TAQMAN® probe). The $10^{th}$ segment may contain a divalent metal cofactor, such as $MgCl_2$. The end of the $9^{th}$ (or $10^{th}$) segment, can be permanently sealed or contain a pressure gate for collecting the products of the amplification reaction to confirm the results of a genotyping test by DNA sequencing or some other test known to those skilled in the art.

For viral RNA isolation and detection, 100 ul of whole blood is loaded into the $1^{st}$ segment. The device can then be closed by a cap and inserted into an analyzer. Sample processing can include the following steps.

(a) Cell depletion and Sample Lysis. All clamps, except the first clamp, are closed on the device. The actuator operably connected with the $1^{st}$ segment is used to adjust the volume of blood to retain about 100 ul in the segment, and then the $1^{st}$ segment is closed using the associated segment clamp. The actuator operably connected with the $2^{nd}$ segment, in whole or in part, compresses the first subsection of the $2^{nd}$ segment to break the peelable seals between the $1^{st}$, $2^{ed}$, and $3^{rd}$ segments and mix the anti-CD4 particles with the sample and quantification standard. Actuators operably connected with the first subsection can alternately compress the subsection to mix the particles with the sample. Then, a magnetic field can be generated by a magnetic source near the $3^{rd}$ segment to capture the particles. By engaging the associated actuators and clamps in that segment/subsection, the cell depleted sample is moved to the $4^{th}$ segment, a clamp is closed above the $4^{th}$ segment to prevent the depleted cells from mixing with the downstream depleted specimen, and then moved to the $5^{th}$ segment to mix the lysis buffer with the cell depleted sample. The mixture in the $4^{th}$ and $5^{th}$ segments is incubated at 50° C. for 2 minutes.

(b) Nucleic Acid Capture. After lysis incubation, the actuators alternately compress their respective segments to agitate and incubate the mixture for 2 minutes at room temperature to facilitate DNA binding to the particles. Then, a magnetic field is generated by a magnetic source near the segment to capture the particles in suspension. The actuators can alternately compress the segment to capture the particles. The actuators and clamps are sequentially opened and closed to move the unbound sample and waste to the waste reservoir.

(c) Wash. A wash process follows the capture process in order to remove residual debris and reaction inhibitors from the particles and the segments that would be used for further sample processing. A dilution-based washing is used with the ethanol wash buffer and a flow-based washing is used with the MES wash buffer. Clamps and actuator first open, and then the actuator closes to move the ethanol buffer to the $6^{th}$ segment, followed by the closing of the clamp. The magnetic field is removed; the actuator and at least one adjacent actuator is alternately compressed against their respective segments to generate flow to re-suspend the particles. The magnetic field is then turned on to capture substantially all the particles and the liquid is moved to a waste reservoir. After completing the first wash, the MES wash buffer is moved from one segment to another and the buffer is manipulated using the sequential application and release of the corresponding actuators and clamps to ensure an essentially laminar flow of the wash buffer through the flow channel. When the wash is completed, the actuators and clamps are closed and substantially all the waste is moved to the waste reservoir.

(d) Nucleic Acid Elution. The elution buffer is moved from the $8^{th}$ segment using a similar process as mentioned before. The magnetic field can be removed and the particles are re-suspended in the elution buffer under flow between the fourth and fifth segments. The particle suspension is incubated at 95° C. under stationary flow or agitation conditions for 2 minutes. The magnetic field is turned on and substantially all the particles are immobilized, and the eluted nucleic acid solution can be moved to the $8^{th}$ segment by sequentially opening and closing the actuators and clamps. The actuators can compress the $8^{th}$ segment to adjust the volume of the eluted nucleic acid solution to 40 ul and a clamp can then close against the device to complete the DNA extraction process.

(e) Nucleic Acid Amplification and Detection. The nucleic acid solution can then be transferred to the $9^{th}$ segment, mixed, and incubated with UNG 280 at 37° C. for 1 minute to degrade any contaminant PCR products that may have been present in the biological sample. After the incubation, the temperature may be increased to 95° C. to denature nucleic acids and UNG for 2 minutes. The nucleic acid solution can then be transferred to the $10^{th}$ segment, and mixed with RT-PCR reagents at 65° C. for 10 minutes, followed by incubation at 60° C. to initiate hot start PCR. A typical 2-temperature, amplification assay of 50 cycles of 95° C. for 2 seconds and 60° C. for 15 seconds can be conducted by setting the $8^{th}$ segment at 95° C. and the 9 segment at 60° C., and transferring the reaction mixture between the segments alternately by closing and opening the associated actuators. A typical 3-temperature, amplification assay of 50 cycles of 95° C. for 2 seconds, 60° C. for 10 seconds, and 72° C. for 10 seconds can be conducted by setting the $8^{th}$ segment at 95° C., $9^{th}$ segment at 72° C. and the $10^{th}$ segment at 60° C., and alternately transferring the reaction mixture among the segments by closing and opening the associated actuators. A detection sensor, such as a photometer, optically connected to the $9^{th}$ chamber can monitor real-time fluorescence emission from the reporter dye through a portion of the device wall. After an assay is complete, the test results are reported.

Example 2. Offline CD4 Depletion and Analysis

Plasma dynamic range was determined using a Roche Cobas® 6800/8800 HIV-quantification calibration panel. The panel components are provided in Table 1 below.

TABLE 1

Roche HIV-1 quantitation calibration panel

| Material | Material N | Concentration | Target | Matrix |
|---|---|---|---|---|
| TR HIV 8E5 CAL PANEL PM1 | 5219612991 | 1.00E+07 Cp/mL | HIV LAV 8E5 | EDTA Plasma |
| TR HIV 8E5 CAL PANEL PM2 | 5219639991 | 1.00E+06 Cp/mL | HIV LAV 8E5 | EDTA Plasma |
| TR HIV 8E5 CAL PANEL PM3 | 5219647991 | 1.00E+05 Cp/mL | HIV LAV 8E5 | EDTA Plasma |
| TR HIV 8E5 CAL PANEL PM4 | 5219655991 | 1.00E+04 Cp/mL | HIV LAV 8E5 | EDTA Plasma |
| TR HIV 8E5 CAL PANEL PM5 | 5219663991 | 1.00E+03 Cp/mL | HIV LAV 8E5 | EDTA Plasma |
| TR HIV 8E5 CAL PANEL PM6 | 5219671991 | 1.00E+02 Cp/mL | HIV LAV 8E5 | EDTA Plasma |
| TR HIV 8E5 CAL PANEL PM7 | 6315801991 | 5.00E+01 Cp/mL | HIV LAV 8E5 | EDTA Plasma |

Figures 2A, 2B:
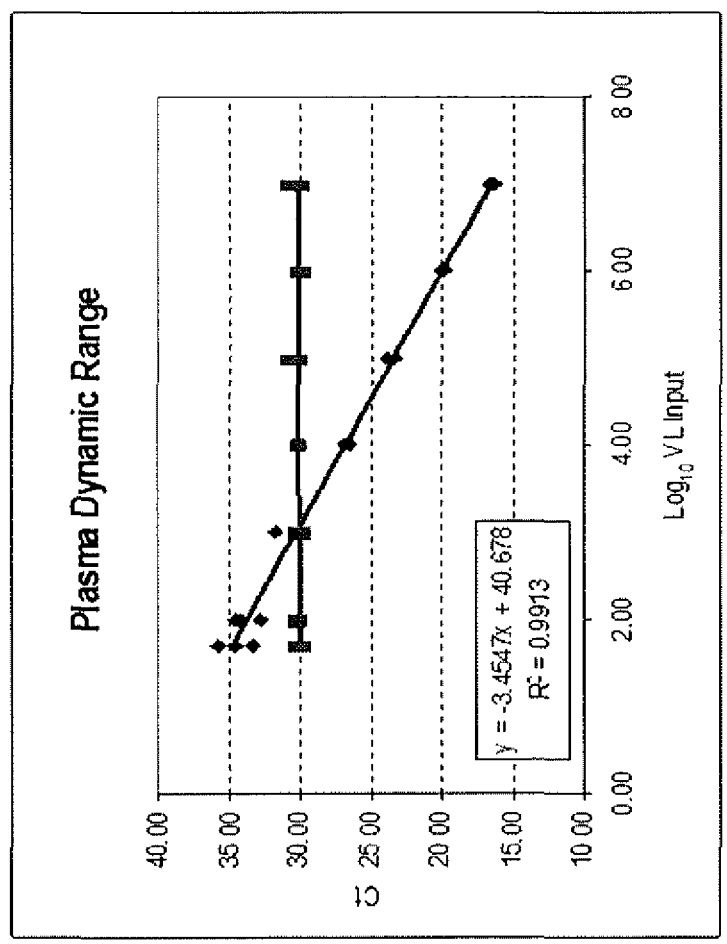
FIGS. 2A-2B show the dynamic range of the Cobas® LIAT® HIV Quantitative assay in plasma.

Three replicates were tested on a Cobas® LIAT® Analyzer for each Roche panel member. To run the tests on the Cobas® LIAT® Analyzer (Roche Molecular Systems, Inc., Pleasanton, Calif.), 100 uL of each panel member material was mixed with 100 uL dilution buffer (1×PBS, 0.1% BSA, 0.1% Sodium Azide), and then the diluted material was added to a Cobas® LIAT® device pre-packaged with assay reagents as described below. The device was analyzed in a Cobas® LIAT® Analyzer and upon completion of the assay, Ct and target input levels were used for dynamic range regression analysis. The results are shown in FIGS. 2A-2B, which show 6 log linearity in plasma and no inhibition of HIV on the quantification standard performance of the assay.

For whole blood dynamic range, the Roche HIV-1 quantitation calibration panel members (see Table 2) were spiked with pooled normal human EDTA whole blood at 1:20 ratio. For example, to make 1 mL whole blood sample with HIV-1 spiked-in, 50 uL of a panel member was combined with 950 uL of normal human whole blood (Bioreclamation IVT, Cat #: HMWBEDTA2), mixed by pipetting. Four test samples were prepared for whole blood dynamic range as shown in Table 2 below.

TABLE 2

Whole blood dynamic range test samples

| Sample | Concentration | Target | Matrix |
|---|---|---|---|
| Sample 1 | 5.00E+05 Cp/mL | HIV LAV 8E5 | EDTA whole blood |
| Sample 2 | 5.00E+04 Cp/mL | HIV LAV 8E5 | EDTA whole blood |
| Sample 3 | 5.00E+03 Cp/mL | HIV LAV 8E5 | EDTA whole blood |
| Sample 4 | 5.00E+02 Cp/mL | HIV LAV 8E5 | EDTA whole blood |

Figure 3B:
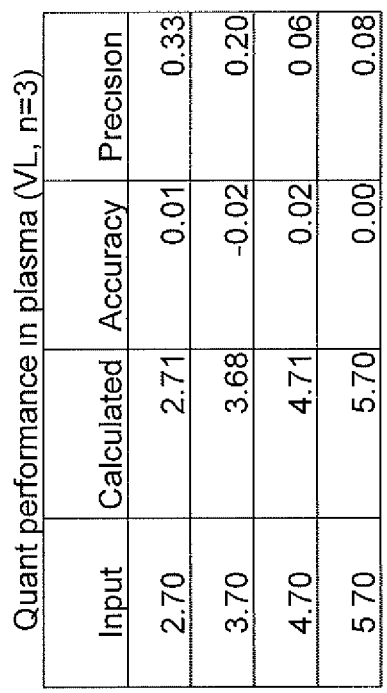
FIGS. 3A-3B show the dynamic range of the Cobas® LIAT® HIV Quantitative assay in whole blood.
Figure 3A:
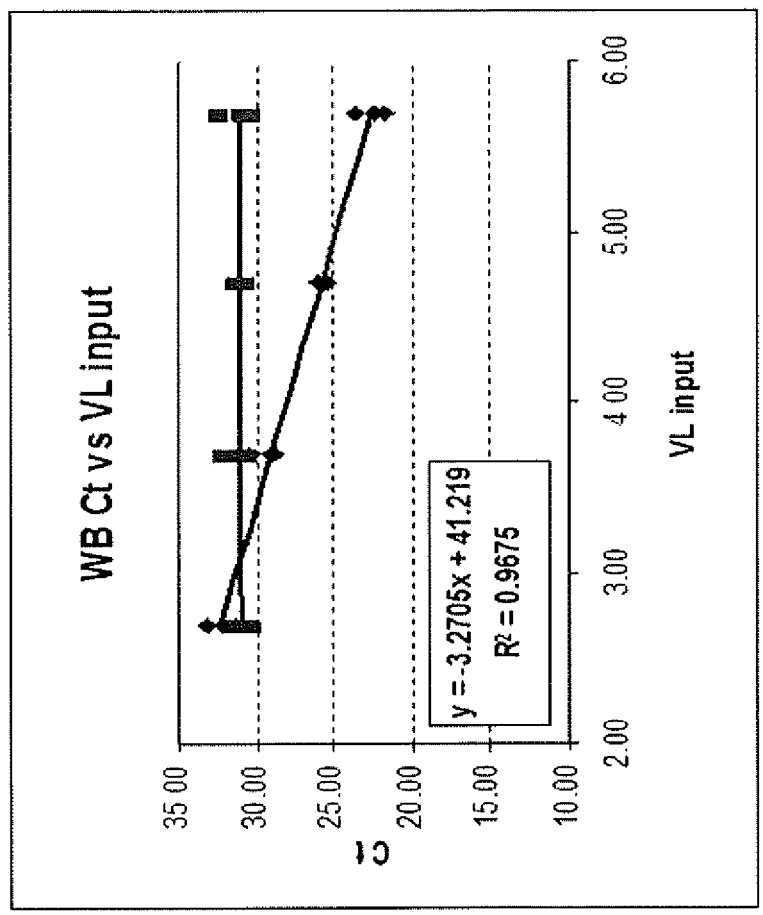

Three replicates were tested on the Cobas® LIAT® Analyzer for each sample. To run the tests on the Cobas® LIAT® Analyzer, 100 uL of a whole blood sample was mixed with 100 μL dilution buffer, and then loaded into a Cobas® LIAT® device prepackaged with other assay reagents packed. The device was analyzed in a Cobas® LIAT® Analyzer and upon completion of the assay, Ct and target input levels were used for dynamic range regression analysis. The results are shown in FIGS. 3A-3B, which show at least 4 log linearity in whole blood and no inhibition of HIV on the quantification standard performance of the assay. In addition, the limits of detection (LOD) of the assay in plasma vs. whole blood are shown in FIG. 4.

For each patient blood sample, viral loads in plasma and whole blood were evaluated, as well as the viral load in whole blood after CD4 antibody cell depletion was determined. To separate plasma from whole blood, 10 mL of whole blood in the VACUTAINER® Lavender blood collection tube (Becton Dickinson & Company Corporation, Franklin Lakes, N.J.), was centrifuged at 1200 g for 10 min on a SORVALL® centrifuge (Thermo Fisher Scientific LLC, Waltham, Mass.) at room temperature. The supernatant (plasma) was transferred to a labeled 50 mL centrifuge tube. In an EPPENDORF® microcentrifuge tube (Eppendorf AG, Hamburg, Germany), 80 uL dilution buffer was added followed by the addition of 100 uL of whole blood sample. Before adding blood sample to the EPPENDORF® microcentrifuge tube, the whole blood sample was mixed by inverting the sample tube until blood becomes homogeneous, followed by pipetting 3-5 times. Blood and dilution buffer were mixed by pipetting 6 times.

CD4 antibody particles were vortexed 15 seconds to resuspend the particles and then twenty (20) uL of CD4 antibody DYNABEADS® magnetic glass particles were added to the EPPENDORF® microcentrifuge tube (100 to 500 ug, depends on type of CD4 antibody particles). The mixture was vortexed 2 times (1 second/time) to mix the sample with particles. The tube is loaded on the Rotator and incubated at room temperature with rotation for 10 minutes (Rotator was set at 60° tilt, and 10 rpm). The tube was placed in a magnetic rack for 1 minute and then all liquid (~200 uL) was transferred to a Cobas® Liat® device. RNA isolation and sequence detection in the depleted sample was accomplished in a tube as described in Example 1, except that the tube did not include particles in the second segment. Instead, the second segment included quantification standard.

For each patient sample, 100 uL of plasma mixed with 100 uL of dilution buffer, 100 uL of EDTA whole blood mixed with 100 uL of dilution buffer, and 100 uL of EDTA whole blood with CD4 antibody cell depletion were loaded on to Cobas® LIAT® device and tested on a Cobas® LIAT® analyzer. Data were collected after test runs finished. Viral load of each sample type was calculated using equations generated in dynamic range regression for plasma or whole blood. Viral load correlation between plasma and whole blood, or plasma and whole blood with CD4 cell depletion were evaluated.

Figure 5:
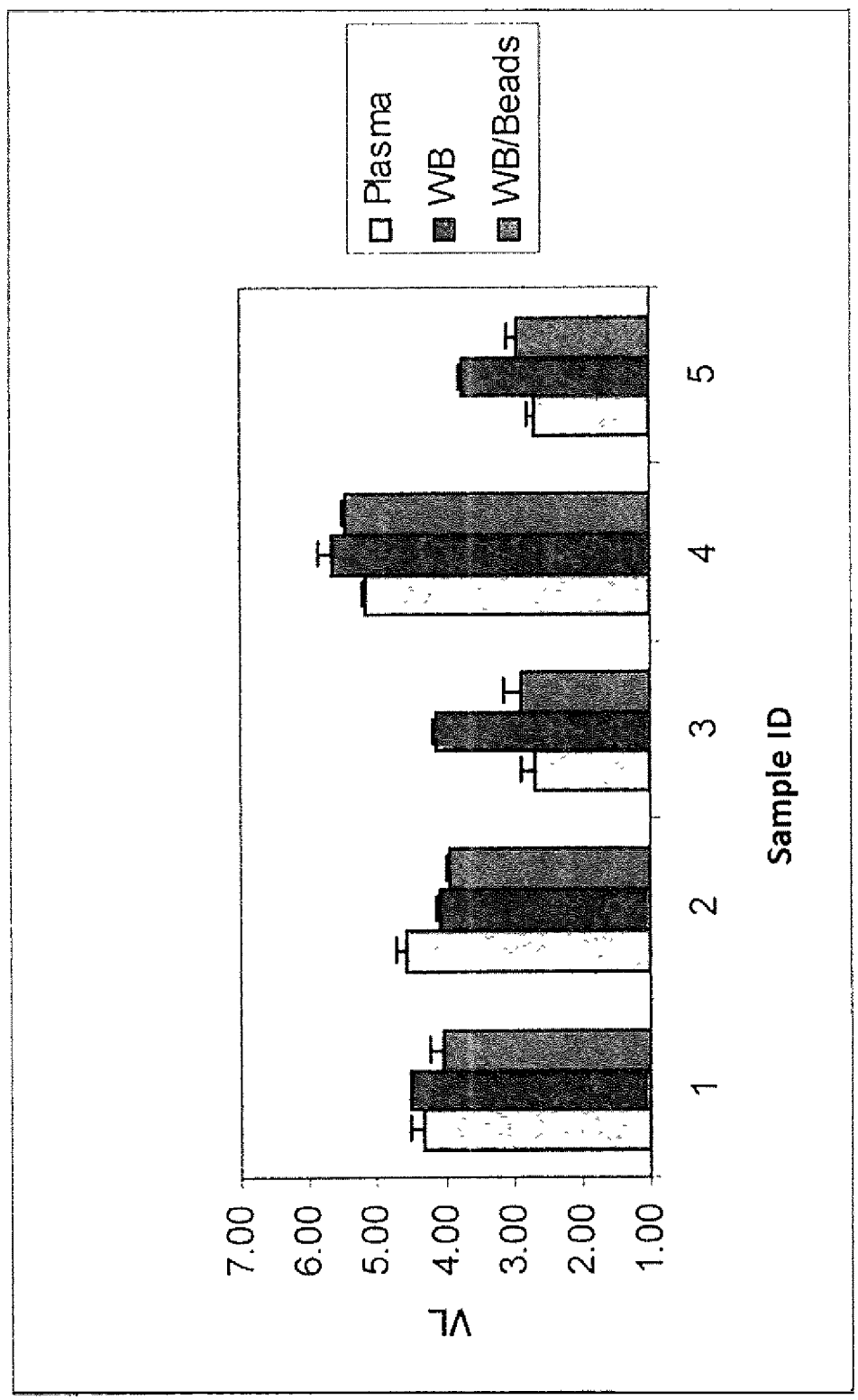
FIG. 5 shows HIV viral load measurements of five patient samples including plasma, whole blood (WB), and whole blood treated with CD4 antibody particles (WB/particles). CD4 antibody particles treatment improved viral load correlation of two samples (numbers 3 and 5).
Figure 6B:
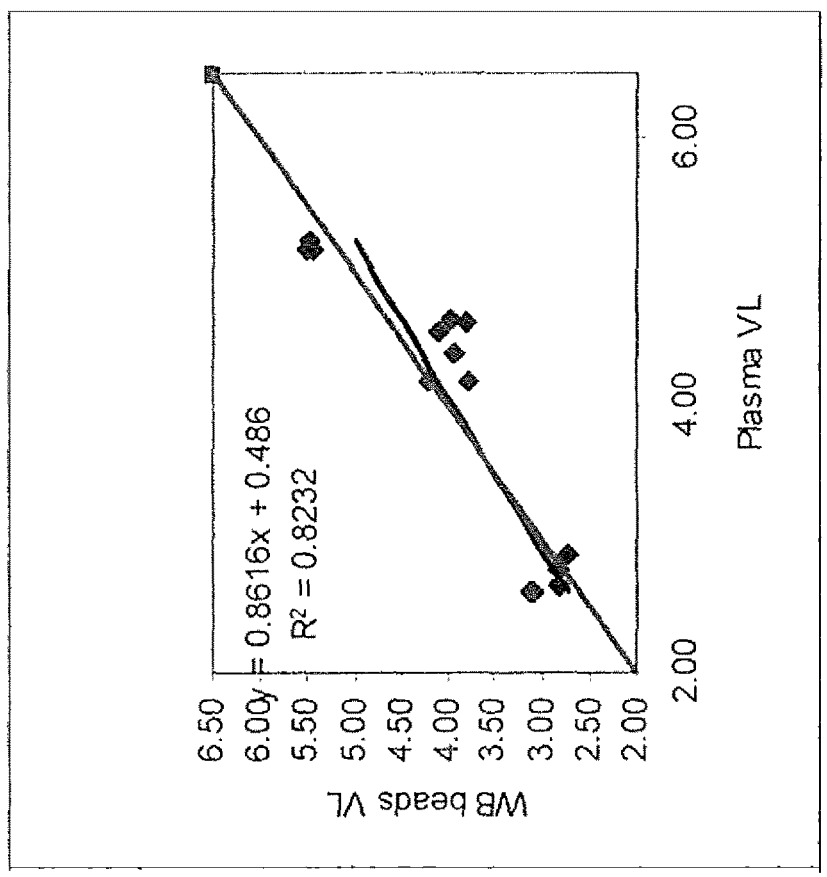
FIGS. 6A-6B show how CD4 antibody particle pre-treatment improves whole blood and plasma viral load correlation.
Figure 6A:
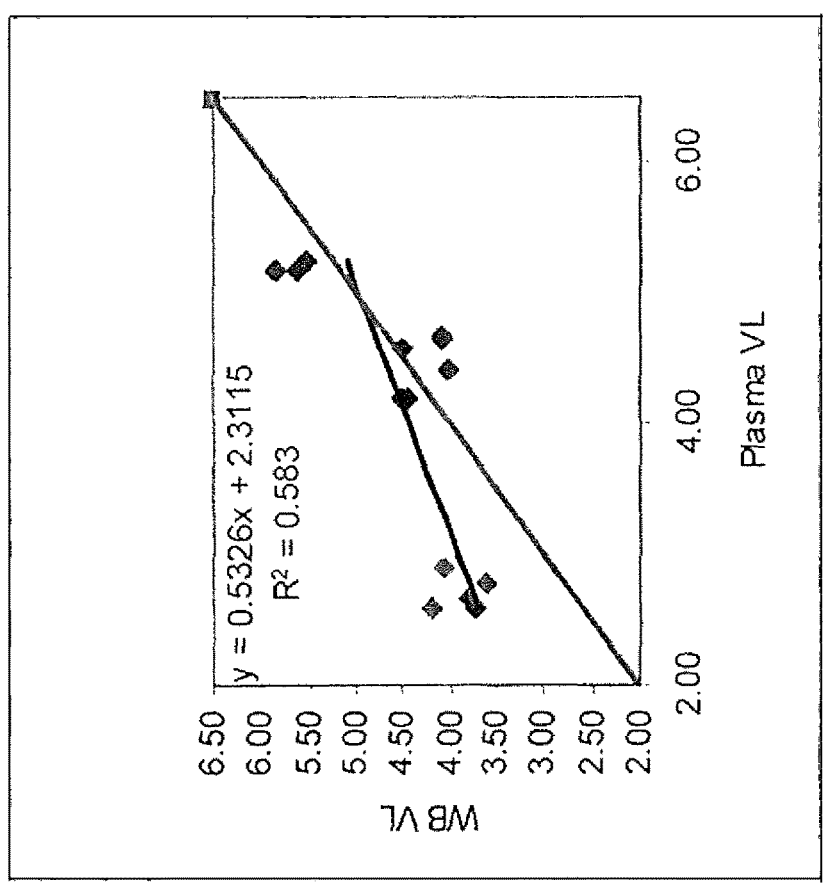

Following the protocol described above, one round of binding with CD4 magnetic particles was able to deplete 96% of CD4 positive cells from unfrozen whole blood samples. The results are shown in Table 3 and FIGS. 5 and 6A-6B. FIG. 5 shows that CD4 depletion treatment improved viral load correlation in samples 3 and 5. FIG. 6A shows the viral load correlation before CD4 depletion and FIG. 6B shows the viral load correlation after treatment.

TABLE 3

Viral load measurement values of 5 patient blood samples

| | VL | | | SD | | |
|---|---|---|---|---|---|---|
| Sample ID | Plasma | WB | WB/Particles | Plasma | WB | WB/Particles |
| 1 | 4.32 | 4.50 | 4.03 | 0.22 | 0.04 | 0.21 |
| 2 | 4.57 | 4.07 | 3.91 | 0.13 | 0.04 | 0.09 |
| 3 | 2.67 | 4.11 | 2.90 | 0.20 | 0.08 | 0.25 |
| 4 | 5.19 | 5.67 | 5.49 | 0.04 | 0.17 | 0.03 |
| 5 | 2.68 | 3.71 | 2.92 | 0.09 | 0.09 | 0.17 |

Out of the five patient samples tested, plasma viral load measurements of two samples were less than 1e3 copies/ml and direct whole blood viral load measurement of the two patient samples were higher than 1e3 copies/ml. Pre-treatment of the two patient whole blood samples with CD4 antibody particles improved whole blood and plasma viral load correlation. Following pre-treatment with anti-CD4 particles, the whole blood viral load of the same two samples previously studied were less than 1e3 copies/ml.

Example 3. Optimized Conditions for CD4 Depletion in a Cobas® LIAT® Device

Various fluid flow driving mechanisms in a tube were evaluated based on the desired degree of cell lysis. As described above, in general, fluid flow is controlled in the device shown in FIG. 1 by compressing selected segments of the tube with a centrally-positioned actuator and its flanking clamps to form a flow channel in the device with a gap (i.e., the diameter of the flow channel) of about 1 to about 500 um (0.001-0.5 mm), e.g., about 5 to 500 um (0.005-0.5 mm). The adjacent actuators gently compress the adjacent segments in liquid communication with the flow channel to generate an offset inner pressure to ensure a substantially uniform gap of the flow channel. It was found that the degree of cell lysis can be modified by varying the gap over a shorter span of the pre-treatment compartment relative to that used to achieve complete cell lysis. Therefore, using this method, cell depletion without cell lysis could be achieved without the use of a filter positioned in the sample pretreatment compartment.

Three different fluid flow mechanisms were designed for use in the sample pre-treatment compartment (i.e., the portion of the device positioned between the sample introduction port and the segment used for nucleic acid capture):

a) conventional lysis fluid flow: low shear mixing with cell lysis;
b) harsh lysis fluid flow: high shear mixing with cell lysis; and
c) cell depletion fluid flow: low shear mixing without cell lysis.

The sample pre-treatment compartment includes a plurality of segments, e.g., up to 5 segments, and for conventional lysis and harsh lysis, each of the segments of the compartment were used such that fluid mixing was performed over the full length of the fluid flow channel in the compartment. In contrast, in order to achieve cell depletion and the subsequent nucleic acid extraction of the cell-depleted sample, a subset of the segments in the compartment can be used, e.g., as few as 3 of the 5 segments or up to all of the segments of the compartment can be used. It was found that the fluid flow mechanism could be performed in fewer segments and the diameter of the flow channel in and between segments during the mixing/lysis process was modified relative to conventional and harsh lysis. The optimized conditions for conventional lysis, harsh lysis, and cell depletion are shown below:

TABLE 4

Relative Actuator Position, Lysis Type & Flow Channel Gap

| Actuator | Conventional Lysis (General Mixing) | Harsh Lysis (Generating Shear Forces) | Cell Depletion without Lysis |
|---|---|---|---|
| P0 | Variable gap, 0-3 mm | Variable gap, 0-3 mm | Variable gap, 0.4-3 mm |
| P1 | Variable gap, 0-3 mm | Variable gap, 0-3 mm | Narrow, fixed gap, 0-1 mm |
| P2 | Variable gap, 0-3 mm | Narrow, fixed gap, 0-.15 mm | Variable gap, 0.4-3 mm |
| P3 | Variable gap, 0-3 mm | Variable gap, 0-3 mm | Closed |
| P4 | Variable gap, 0-3 mm | Variable gap, 0-3 mm | Closed |

In order to achieve conventional lysis (shown in column 2 of the table), the actuators and clamps were selectively engaged/disengaged to move liquid in the flow channel throughout the pre-treatment compartment. In order to achieve harsh lysis, the innermost segment of the flow channel (P2) was held to a narrower, fixed gap relative to the gaps flanking the inner segment, thereby subjecting the fluid in that inner segment of the flow path to shear forces that generated relatively harsh lysis conditions. The gap of the innermost segment was substantially reduced and held fixed relative to that in the flanking segments, i.e., 0.15 mm in P2 versus up to 3 mm in P0-P1 and P3-P4. By contrast, in order to achieve cell depletion without cell lysis, the entire mixing step could be performed over a shorter fluid flow channel including fewer segments of the device (e.g., P0-P2), and the innermost segment was compressed to a gap of up to 1.1 mm, which is about one-third the size of the gap in the flanking segments, thereby achieving a gentle mixing that does not result in cell lysis. In one embodiment, the gap can be reduced by 25-50% of the diameter of the channel in the flanking segments, e.g., 33% of the diameter.

The process is illustrated in FIGS. 7A-7D. A portion of the sample processing device is illustrated in FIG. 7A, in which the tube 701 includes a sample pre-treatment compartment 702 comprising a plurality of segments 703-707 in fluid communication with the remainder of the segments in the sample processing device 708. A fluid flow channel 709 spans the pre-treatment compartment into the remainder of the segments of the sample processing device. When the actuators (P0-P4) and clamps (C0-C5) in communication with the pre-treatment compartment are not engaged with the tube, the fluid flow channel has a diameter of about 5 mm, but when the tube is positioned in the device, the motors (not shown) controlling the position of the actuators and clamps drive the actuators and clamps against the outer walls of the tube, slightly compressing the tube such that the fluid flow channel has a diameter of about 3 mm, which is designated as the fully open position of the compartment. FIG. 7B shows the relative dimensions of the fluid flow channel during conventional lysis; the fluid flow channel spans P0-P5 and the channel has a diameter of up to 3 mm. FIG. 7C shows the relative dimensions of the fluid flow channel during harsh lysis; the fluid flow channel spans P0-P5, with the innermost segment, P2, reduced to a diameter of up to 0.15 mm. Therefore, during harsh lysis, the fluid flow is subjected to high pressure in P2 relative to the flanking segments, introducing high shear forces that lead to harsh cell lysis. In contrast, FIG. 7D shows the relative dimensions of the fluid flow channel during cell depletion; the fluid flow channel spans P0-P2, with the diameter of the channel in the innermost segment, P1, being reduced from up to 3 mm (in P0 and P2) to up to 1.1 mm. The innermost channel is not compressed to the same degree as it is during harsh lysis, resulting in a more gentle mixing cycle that does not lyze the cells in the fluid.

In addition to the altered fluid flow mechanism, the speed of the motors operatively connected with each of the actuators and clamps was adjusted to avoid cell lysis during cell depletion. During conventional and harsh lysis, each of the motors engaged with the actuators and clamps rapidly engage and disengage the actuators and clamps at an equal rate. However, in order to achieve cell depletion without cell lysis, the motor speed during disengagement was adjusted so that the motor logarithmically decelerates relative to the rate of acceleration. This is illustrated in FIGS. 8A-8B, wherein FIG. 8A shows the movement of the motor during conventional and harsh lysis and FIG. 8B show the movement of the motor during cell depletion.

The methods described herein and in Example 1 were used to evaluate the viral load of patient samples in a sample processing device and the results are shown below:

TABLE 5

Viral Load Testing in a Device Configured to Perform Cell Depletion

| | | VL | |
| --- | --- | --- | --- |
| Sample ID | Sample type | Ave Log VL | Ave VL (cp/mL) |
| 1 | Blood | 3.14 | 1403 |
| 1 | Blood/AB beads | 2.36 | 244 |
| 2 | Blood | 3.24 | 1738 |
| 2 | Blood/AB beads | 2.43 | 368 |
| 3 | Blood | 3.59 | 4102 |
| 3 | Blood/AB beads | 2.40 | 349 |

The results shown in Table 5 are similar to those achieved using offline processing, described in Example 2.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed:

1. A device configured to perform a quantitative PCR analysis of one or more viral or tumor target oligonucleotide sequences in a whole blood sample comprising a plurality of cells including a cell surface marker for a virus or tumor, said device comprising a tube defining a fluid flow channel and a plurality of segments positioned therein, said device including
   a. a first set of segments in said fluid flow channel defining a sample pre-treatment compartment comprising, from a proximate to a distal end, a first flanking segment, an inner segment, and a second flanking segment, and anti-cell surface marker antibodies immobilized on a surface in one or more of said segments, wherein said sample pre-treatment compartment does not include a filter;
   b. a second set of segments in said fluid flow channel defining a PCR analysis region adjacent to said sample pre-treatment compartment, said PCR analysis region comprising one or more additional segments each configured to conduct one or more steps of said PCR analysis comprising reagent preparation, target enrichment, inhibitor removal, nucleic acid extraction, amplification and real-time detection; and
   c. a plurality of compression members operably connected with said plurality of segments and configured to selectively compress one or more segments of said sample pre-treatment compartment to form a flow channel in the sample pre-treatment compartment such that the inner segment flow channel diameter is less than the diameter of the flow channel in the first and second flanking segments;
   wherein said device is configured to generate a depleted sample in the sample pre-treatment compartment comprising <5% cells including said cell surface marker.

2. The device of claim 1 wherein said inner segment flow channel diameter is between 25-50% of the diameter of the flow channel in the first and second flanking segments.

3. The device of claim 1 wherein said inner segment flow channel diameter is about 33% of the diameter of the flow channel in the first and second flanking segments.

4. The device of claim 1 wherein said device has a limit of detection of <100 copies/mL of virus or tumor.

5. The device of claim 1 wherein said cell surface marker is selected from the group consisting of CD4, CD45, beta-microglobulin, or mixtures thereof.

6. A method of conducting a quantitative analysis of a whole blood sample for viral or tumor load using a device according to claim 1, wherein said whole blood sample comprises a plurality of cells including a cell surface marker for a virus or tumor, said method comprising
   a. adding said whole blood sample to said device of claim 1;
   b. mixing said surface and sample in said device to form said depleted sample under conditions that do not lyse cells in said sample; and
   c. measuring, in said device, the viral or tumor load in said depleted sample.

7. The method of claim 6 wherein said inner segment flow channel diameter is between 25-50% of the diameter of the flow channel in the first and second flanking segments.

8. The method of claim 6 wherein said inner segment flow channel diameter is about 33% of the diameter of the flow channel in the first and second flanking segments.

9. The method of claim 6 wherein said surface of said device is an inner wall of said pre-treatment compartment.

10. The method of claim 6 wherein said depleted sample comprises <2.5% cells including said cell surface marker.

11. The method of claim 6 wherein said depleted sample comprises <1% cells including said cell surface marker.

12. The method of claim 6 further comprising separating, in said device, said depleted sample from said surface following step (b).

13. The method of claim 6 wherein said method achieves a limit of detection of <100 copies/mL of virus or tumor.

14. The method of claim 6 wherein said cell surface marker is selected from the group consisting of CD4, CD45, beta-microglobulin, or mixtures thereof.

15. The method of claim 6 wherein said cell surface marker is CD4.

16. The method of claim 6 wherein said viral or tumor load measurement is linearly related to a viral or tumor load measurement, respectively, in a plasma sample taken from a patient providing said whole blood sample.

\* \* \* \* \*